US011679009B2

(12) United States Patent
Ryschka et al.

(10) Patent No.: US 11,679,009 B2
(45) Date of Patent: Jun. 20, 2023

(54) ORTHESIS OR PROSTHESIS SYSTEM AND METHOD FOR OPEN-LOOP OR CLOSED-LOOP ORTHESIS OR PROSTHESIS CONTROL

(71) Applicant: Ottobock SE & Co. KGaA, Duderstadt (DE)

(72) Inventors: Martin Ryschka, Stockelsdorf (DE); Roman Kusche, Hamburg (DE)

(73) Assignee: Ottobock SE & Co. KGaA, Duderstadt (DE)

( * ) Notice: Subject to any disclaimer, the term of this patent is extended or adjusted under 35 U.S.C. 154(b) by 77 days.

(21) Appl. No.: 17/045,613

(22) PCT Filed: Apr. 1, 2019

(86) PCT No.: PCT/EP2019/058135
§ 371 (c)(1),
(2) Date: Oct. 6, 2020

(87) PCT Pub. No.: WO2019/197189
PCT Pub. Date: Oct. 17, 2019

(65) Prior Publication Data
US 2021/0161685 A1 Jun. 3, 2021

(30) Foreign Application Priority Data

Apr. 9, 2018 (DE) ..................... 10 2018 205 306.5

(51) Int. Cl.
*A61F 2/72* (2006.01)
*A61B 5/053* (2021.01)
(Continued)

(52) U.S. Cl.
CPC ................ *A61F 2/72* (2013.01); *A61B 5/053* (2013.01); *A61B 5/397* (2021.01); *A61B 5/4851* (2013.01);
(Continued)

(58) Field of Classification Search
None
See application file for complete search history.

(56) References Cited

U.S. PATENT DOCUMENTS

| 4,808,187 A | 2/1989 | Patterson et al. |
| 8,828,093 B1 | 9/2014 | Kuiken et al. |
| 2012/0004736 A1 | 1/2012 | Goldfarb et al. |

FOREIGN PATENT DOCUMENTS

| CN | 105771182 A | * 7/2016 | ............. A61B 5/389 |
| DE | 10 2007 013 660 A1 | 9/2008 | |

(Continued)

OTHER PUBLICATIONS

International Search Report for International Application No. PCT/EP2019/058135, dated Apr. 1, 2019, 8 pages.

*Primary Examiner* — David H Willse
(74) *Attorney, Agent, or Firm* — Holland & Hart LLP (57) ABSTRACT

An orthosis or prosthesis system comprising at least one orthosis or prosthesis, at least one pair of electrodes for contacting the body of the user of the orthosis or prosthesis in order to capture muscle-related signals, at least one evaluation unit for muscle-related signals captured by the at least one electrode pair, at least one actuator for moving the at least one orthosis or prosthesis, and at least one control unit for controlling the at least one actuator. The at least one electrode pair is designed to capture at least a first muscle-related signal using a first measurement frequency and a second muscle-related signal using a second measurement frequency. The at least one evaluation unit evaluates a phase of the first signal and a phase of the second signal. The muscle-related signals can be bioimpedance signals. The system makes it possible to distinguish between muscle contractions and interfering signals.

20 Claims, 3 Drawing Sheets

(51) Int. Cl.
*A61B 5/397* (2021.01)
*G06F 3/01* (2006.01)
*A61B 5/00* (2006.01)
A61F 2/70 (2006.01)
A61F 2/50 (2006.01)
A61F 2/76 (2006.01)
A61F 2/68 (2006.01)
A61F 5/01 (2006.01)

(52) U.S. Cl.
CPC ...... *G06F 3/015* (2013.01); *A61F 2002/5059* (2013.01); *A61F 2002/6827* (2013.01); *A61F 2002/701* (2013.01); *A61F 2002/704* (2013.01); *A61F 2002/765* (2013.01); *A61F 2005/0155* (2013.01)

(56) References Cited

FOREIGN PATENT DOCUMENTS

| EP | 3 000 391 A1 | 3/2016 |
| WO | 2013029619 A1 | 3/2013 |
| WO | 2017160183 A1 | 9/2017 |

\* cited by examiner

ORTHESIS OR PROSTHESIS SYSTEM AND METHOD FOR OPEN-LOOP OR CLOSED-LOOP ORTHESIS OR PROSTHESIS CONTROL

CROSS REFERENCE TO RELATED APPLICATIONS

This application is a U.S. National Entry and claims priority to PCT International Patent Application No. PCT/EP2019/058135, filed 1 Apr. 2019, and entitled "ORTHESIS OR PROSTHESIS SYSTEM AND METHOD FOR OPEN-LOOP OR CLOSED-LOOP ORTHESIS OR PROSTHESIS CONTROL", which claims priority to Germany Patent Application No. 10 2018 205 306.5 filed 9 Apr. 2018, the entire disclosures of which are incorporated herein by this reference.

TECHNICAL FIELD

The invention relates to an orthosis or prosthesis system and a method for open-loop or closed-loop control of an orthosis or prosthesis by way of such a system.

Within the meaning of the invention, an orthosis is an aid that is used to stabilize, unburden, immobilize, guide or correct a body part. Within the meaning of the invention, a prosthesis is an aid that replaces a body part.

BACKGROUND

Consequently, orthoses and prostheses are used in medicine as supplementary aids or as a replacement for limbs and organs. Conceptually, orthoses and prostheses are not always separable, especially since some orthoses also replace lost body functions. Therefore, reference is always made to "orthoses or prostheses" below. It is naturally possible to also apply the subject matter of the invention only to a prosthesis or only to an orthosis.

Starting point for deliberations in respect of open-loop or closed-loop orthosis or prosthesis control is the desire of the user of an orthosis or prosthesis to perceive the latter not as a disadvantage or impediment but to be able to employ it in daily use, as a support or unburdening of the body part to be controlled in the case of an orthosis or as a complete replacement as possible for the missing body part in the case of a prosthesis.

Consequently, the orthosis or prosthesis system should compensate the limitations of the user to the best possible extent or create a replacement which prevents limitations.

Therefore, the demands on an orthosis or prosthesis system include, for example, the preservation or reestablishment of the motor capabilities of the user and the suitability for everyday life. Here, as in many degrees of freedom of movement as possible allow the user to compensate limitations particularly well.

In an orthosis or prosthesis system within the meaning of the invention, the orthosis or prosthesis is combined with a sensor system and an actuator system, which can be inserted together into a control procedure or else a control loop.

Here, sensor system and actuator system is understood to mean the detection of signals or the trigger of movements by signals, as is conventional.

For the open-loop or closed-loop control of orthoses or prostheses, the desire of the user to undertake a movement must be ascertained as quickly and as reliably as possible. This is usually implemented by detecting muscle-related signals. Here, muscle-related signals are understood to mean signals, in particular electrical signals, which relate to a state of a muscle, in particular to the strength and/or direction of the contraction of the muscle or to the direction and/or speed of the movement of the muscle.

The disturbance resistance of the captured muscle-related signals used for the closed-loop control is particularly important in this case in order to prevent malfunctions of the orthosis or prosthesis system.

The prior art has disclosed various methods for detecting muscle-related signals, which can be used for open-loop or closed-loop control of orthoses or prostheses:

DE 10 2008 002 933 A1 discloses a recording of data for patient analysis, as can be used in conventional prostheses. Here, the electrical activity of muscles or muscle groups is detected and analyzed at a few locations, usually two locations, by means of various surface electrodes, for example by way of electromyography (EMG).

Mechanomyography (MMG), which measures vibrations that arise when a muscle tenses, is a further known process for detecting muscle activities. Prior scientific publications furthermore show that even the magnitude of the complex electrical bioimpedance is influenced by muscle contractions (cf. Soo-Chan Kim: Estimation of Hand Gestures Using EMG and Bioimpedance, The Transactions of the Korean Institute of Electrical Engineers, vol. 65, no. 1, pp. 194-199, 2016, ISSN 1975-8359 (print)/ISSN 2287-4364 (online), http://dx.doi.org/10.5370/KIEE.2016.65.1.194), wherein the discussion is restricted to the manner of possible measurements with sensors or electrodes and the interpretation of measurement results.

SUMMARY

The invention is based on the object of providing an orthosis or prosthesis system and a method for open-loop or closed-loop control of an orthosis or prosthesis by such a system, which each have an improved disturbance resistance.

In particular, it is desirable to be able to differentiate between disturbance influences and actual muscle contraction to the best possible extent.

This object is achieved by an orthosis or prosthesis system and an open-loop or closed-loop control method. Advantageous embodiments of the invention are disclosed herein.

The considered orthosis or prosthesis system has the following components: at least one orthosis or prosthesis, at least one pair of electrodes provided for contacting the body of the user of the orthosis or prosthesis for the purposes of detecting muscle-related signals, at least one evaluation unit for muscle-related signals detected by the at least one electrode pair, at least one actuator for moving the at least one orthosis or prosthesis, and at least one control unit for controlling the at least one actuator.

According to a first aspect of the invention, the at least one electrode pair is configured to detect at least a first muscle-related signal using a first measurement frequency and a second muscle-related signal using a second measurement frequency. Moreover, the at least one evaluation unit is configured to evaluate a phase of the respective first signal and a phase of the respective second signal. The evaluation of the phase of the respective first signal and the phase of the respective second signal can render it possible to distinguish between a "genuine" muscle-related signal and a disturbance signal.

In a preferred embodiment of the invention, the respective evaluation unit is configured to evaluate a phase progression of the respective first and respective second signal. As will be described below, the phase progression of a muscle-related signal can have certain characteristics that do not occur in the case of a disturbance signal. This allows a "genuine" muscle-related signal to be distinguished from any other type of signal, which is referred to as disturbance signal here.

In a preferred embodiment of the invention, the respective evaluation unit is configured to compare a phase of the respective first signal to a reference phase, in particular to a frequency-dependent reference phase, in order to at least qualitatively ascertain a first phase change to compare a phase of the respective second signal to the reference phase, in particular to the frequency-dependent reference phase, in order to at least qualitatively ascertain a second phase change and to evaluate the first phase change and the second phase change, in particular to compare these to one another.

As a result, the characteristics of a genuine muscle-related signal and of a disturbance signal can be identified and evaluated.

In a preferred embodiment, the reference phase is a phase, in particular a phase determined in advance, which substantially corresponds to a measurement in a relaxed state of a muscle.

The use of such a reference phase can contribute to the signals being identified correctly.

According to a preferred embodiment, the evaluation unit is configured to ascertain whether the first phase change is a phase change in the same direction as the second phase change or in an opposite direction thereto.

The directions of the first and second phase change can be used to distinguish between genuine muscle-related signals and disturbance signals.

According to one embodiment, the evaluation unit is configured to assess the first and second signal as belonging to a muscle contraction if the first and second phase change are phase changes in opposite directions.

This allows a genuine muscle-related signal to be reliably identified.

Accordingly, the evaluation unit can be configured according to one embodiment to assess the first and second signal as belonging to a disturbance if the first and second phase change are phase changes in the same direction.

This allows a disturbance or a disturbance signal to be identified correctly.

According to one embodiment, the first measurement frequency is more than approximately 60 kHz and the second measurement frequency is less than approximately 60 kHz.

The inventors have discovered that the phase progression below a frequency of approximately 60 kHz differs from the phase progression above a frequency of approximately 60 kHz depending on whether the signal to be evaluated is a genuine muscle-related signal or a disturbance signal. Thus, a reliable distinction can be made in the case of a measurement above and below 25 approximately 60 kHz.

According to a preferred embodiment, the first measurement frequency is substantially greater than 60 kHz and/or the second measurement frequency is substantially less than 60 kHz. As a result, the two types of signals can be distinguished with an even greater reliability.

In a preferred embodiment of the invention, the at least first and second muscle-related signal is a (complex) bioimpedance signal.

The above-described characteristic phase behavior occurs in a bioimpedance signal, in particular.

In a preferred embodiment of the invention, the at least one electrode pair is further configured to supply electrical stimulation signals to the user of the orthosis or prosthesis. Using the same electrode pair as for the signal measurement in turn reduces the equipment outlay and ensures that the stimulation signals are supplied precisely to the measurement location of the signal measurements and consequently implemented in the region of the same muscle, to which the signal measurements also relate.

In a preferred variant of this embodiment, the electrical stimulation signals are configured to provide the user of the orthosis or prosthesis with feedback about the movements and/or the state of the orthosis or prosthesis. Movement or state parameters that can relate to the feedback are the speed of the orthosis or prosthesis or the force generated thereby, in particular. By way of example, this can communicate to the user of a hand prosthesis the force with which the prosthesis grasps.

Modular retrofitting of existing orthosis or prosthesis systems is possible.

Consequently, the orthosis or prosthesis system according to the invention is employable in very different applications in medical technology.

In particular, the invention facilitates an improvement in the disturbance resistance of the orthosis or prosthesis control by detecting at least two muscle-related signals with different measurement frequencies. Since the two signals can be detected by the same electrode pair, it is possible to reduce the equipment outlay and ensure that the two signals are measured at exactly the same location.

A second aspect of the invention relates to an orthosis or prosthesis system, comprising at least one orthosis or prosthesis, at least one pair of electrodes provided for contacting the body of the user of the orthosis or prosthesis for the purposes of detecting muscle-related signals, at least one evaluation unit for muscle-related signals detected by the at least one electrode pair, at least one actuator for moving the at least one orthosis or prosthesis, and at least one control unit for controlling the at least one actuator, characterized in that the at least one electrode pair is configured to detect at least a first muscle-related signal using a first measurement frequency and the at least one evaluation unit is configured to evaluate a phase of the first signal.

Even though measuring two signals using different measurement frequencies in accordance with the first aspect of the invention is considered particularly reliable by the inventors, the measurement of only one signal, i.e., with only one measurement frequency, and a subsequent evaluation of the phase of the measured signal may be sufficient under certain circumstances.

Here, it is preferable for the first measurement frequency to be substantially greater than 60 kHz and/or for the evaluation unit to be configured to compare a phase of the first signal to a reference phase, in particular a frequency-dependent reference phase, in order to at least qualitatively ascertain a first phase change.

This allows the distinction between genuine muscle-related signals and disturbance signals to be implemented with sufficient reliability using only one measurement.

In a method according to the invention for open-loop or closed-loop control of an orthosis or prosthesis by an orthosis or prosthesis system according to the invention, at least a first muscle-related signal, preferably a first and a second muscle-related signal, is/are detected by the at least one electrode pair and the phase thereof is evaluated by the at least one evaluation unit. Moreover, the at least one actuator is controlled on the basis of the result of the evaluation of the phase of the at least first muscle-related signal, preferably the phases of the at least first and second muscle-related signal, and the orthosis or prosthesis is moved by way of the at least one actuator.

The method according to the invention can provide quick and simple signal processing for an orthosis or prosthesis system according to the invention.

In addition to conventional orthotics and prosthetics, the method and system presented here can also find use in the control of information technology, such as a PC, games console, or the like, in order to simplify/facilitate the operation thereof for the user. The signals obtained from the human muscle can also be used, in conjunction with a mechatronic device, for electromechanical strengthening of the muscular system.

BRIEF DESCRIPTION OF THE DRAWINGS

Further features, advantages and application options of the invention emerge from the following description in conjunction with the respective figure. In detail.

DETAILED DESCRIPTION

Figure 1:
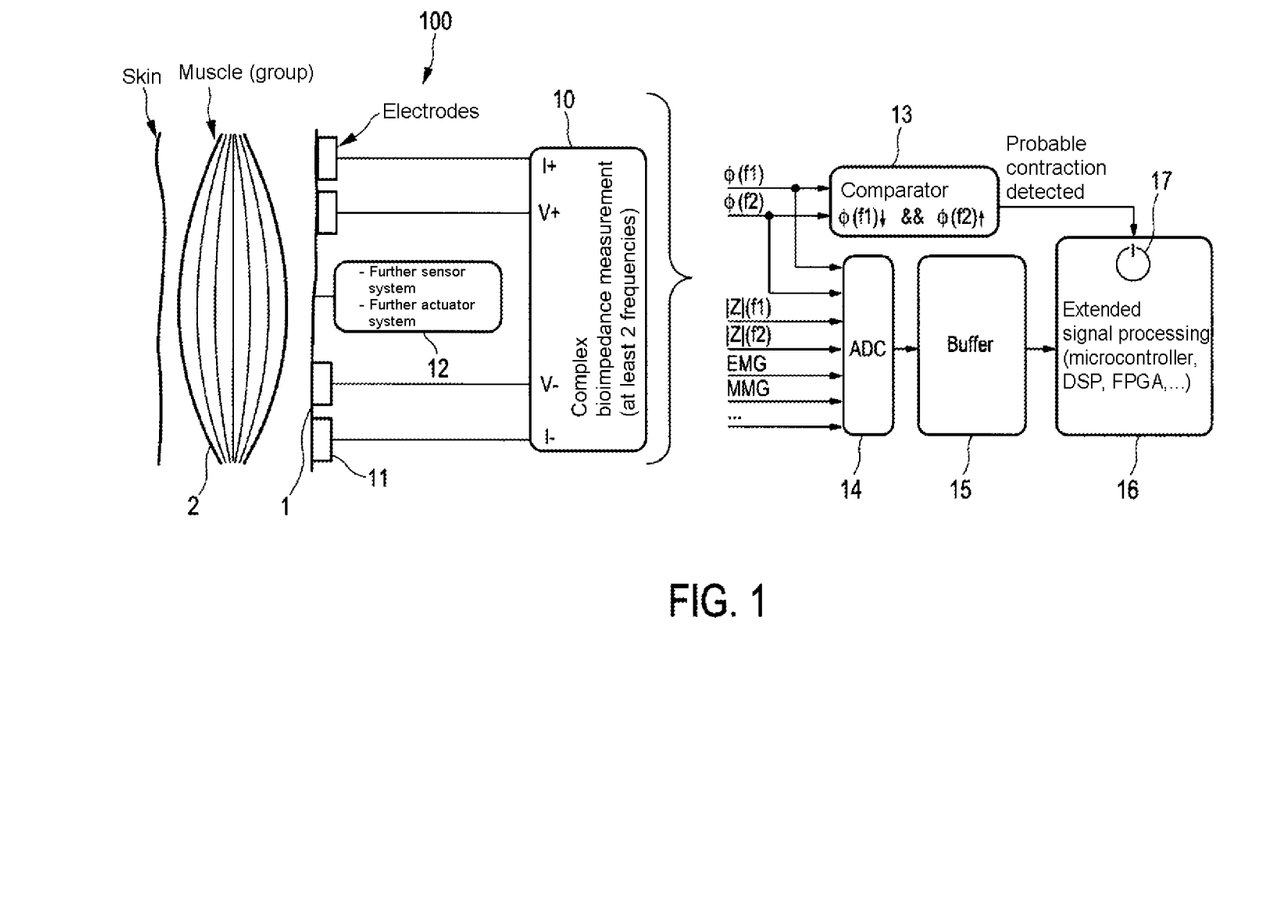
FIG. 1 shows a schematic illustration of a part of an orthosis or prosthesis system according to one embodiment.

FIG. 1 shows part of an orthosis or prosthesis system 100 according to one exemplary embodiment of the present invention. Indicated at the left of FIG. 1 is an arm with skin 1 and muscle 2. Even though the system according to the invention is predominantly described with reference to an arm, it is self-evident that the orthosis or prosthesis system can also be used with other body parts. It is also understood that the muscle 2 described here is a representative of muscles or muscle groups.

A set of electrodes 11 of the orthosis or prosthesis system 100 contacts the skin 1, wherein the electrode set consists of four electrodes 11 in the example shown, specifically in each case two electrodes serving to introduce a current and two electrodes for measuring a voltage. The bioimpedance can be ascertained in a manner known per se from the measured voltage and the measured current or the current known in advance.

The orthosis or prosthesis itself is not shown in FIG. 1. If need be, as shown in FIG. 1, a further sensor system and/or further actuator system 12 may be present and contact the skin 1 where necessary.

The electrodes 11 are connected to an evaluation unit 10, where the current and voltage signals can be processed further and/or stored. The right-hand part of FIG. 1 schematically illustrates the further processing of the current and voltage signals or the further processing of signals derived from the current and voltage signals. These functions can be implemented either in the evaluation unit 10 or in an evaluation unit, not illustrated, coupled thereto.

As will be explained in more detail below, it is possible, in particular, to ascertain and further process the phase $\varphi$ and the absolute value $|Z|$ of the bioimpedance Z. Optionally, as indicated in FIG. 1, it is also possible to ascertain and possibly further process further measurement variables, such as an electromyography (EMG) and/or mechanomyography (MMG) signal.

The inventors have recognized that both the absolute value $|Z|$ and the phase $\varphi$ of the bioimpedance changes in the case of a muscle contraction. In the process, they have determined that the phase change has a characteristic depending on the measurement frequency and said characteristic can be used to distinguish between "genuine" muscle-related signals and disturbance signals. Here, the phrase "genuine" muscle-related signals is preferably understood to mean that this relates to signals which can be traced back to an actually occurring muscle contraction or the like. In contrast thereto, disturbance signals are preferably those signals which can be traced back, at least in part, preferably predominantly, and further preferably substantially exclusively, to disturbance influences. By way of example, such a disturbance influence can be an insufficient contact between an electrode 11 and the skin 1.

Figure 2:
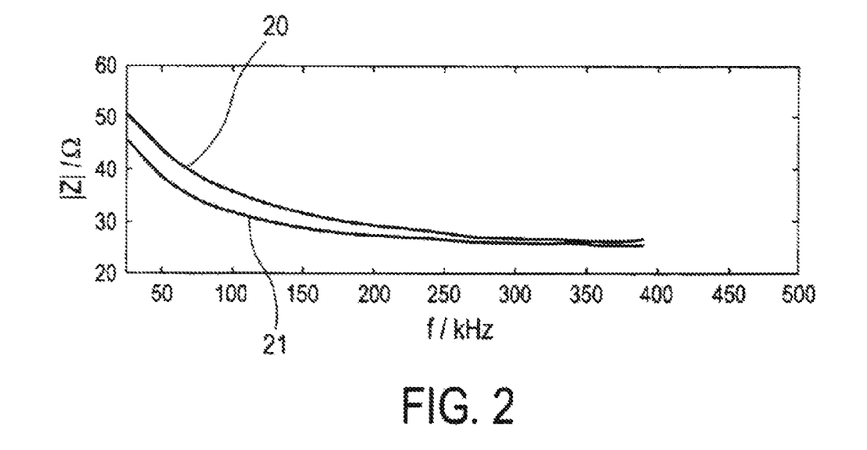
FIG. 2 shows the curve of the absolute value of a bioimpedance signal at different measurement frequencies.

FIG. 2 shows, in exemplary fashion, the frequency response of the absolute value $|Z|$ of the bioimpedance as a function of the employed measurement frequency f for a body part. Here, the upper curve 20 shows the profile of the absolute value $|Z|$ of the bioimpedance in a relaxed state of the muscle and the lower curve 21 shows the profile of the absolute value $|Z|$ of the bioimpedance in the case of a muscle contraction. As clearly shown in FIG. 2, the absolute value $|Z|$ of the bioimpedance reduces over the entire illustrated frequency range in the case of a muscle contraction.

Figure 3:
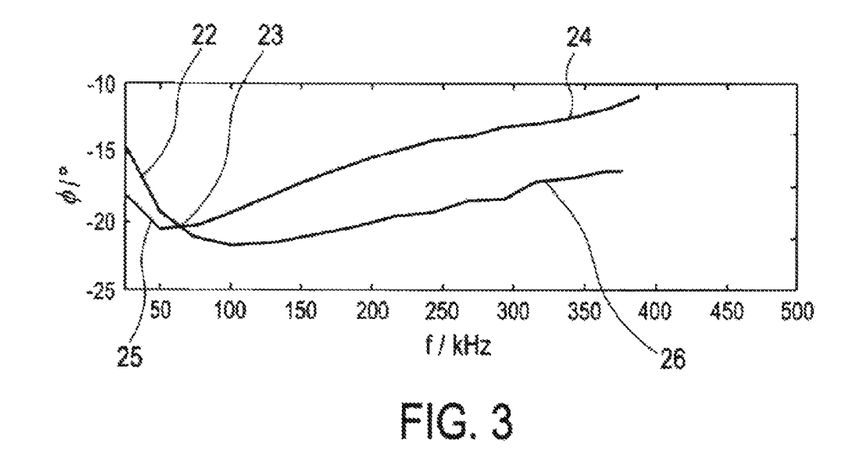
FIG. 3 shows the curve of the phase of a bioimpedance signal at different measurement frequencies.

The phase $\varphi$ of the bioimpedance illustrated in FIG. 3 has a different profile over the frequency range shown. The curve corresponding to a relaxed muscle state is provided with the reference sign 22 in a left-hand region and provided with the reference sign 26 in a right-hand region. The curve sections 25 and 24 represent the phase of the bioimpedance during a muscle contraction. As is clearly evident from FIG. 3, the curve 22, 26 intersects the curve 24, 25 at a point 23. This means that the phase due to a muscle contraction does not change in relation to the relaxed state at a measurement frequency corresponding to the point of intersection 23 (approximately 60 kHz). At lower measurement frequencies (to the left of the point of intersection 23), the phase $\varphi$ of the bioimpedance reduces on account of a muscle contraction. By contrast, the phase $\varphi$ increases at higher measurement frequencies (to the right of the point of intersection 23) as a result of a muscle contraction.

In respect of FIG. 3 (and also accordingly in respect of FIG. 5 explained below), it should be noted that a reduction in the phase in this case means that the phase becomes "even more negative". Thus, the absolute value of the phase increases in the case of the reduction in the phase elucidated in FIG. 3.

The frequency response of the phase $\varphi$ of the bioimpedance, illustrated in FIG. 3, can be evaluated according to exemplary embodiments of the present invention in order to identify a muscle contraction and, in particular, in order to distinguish the latter from a disturbance signal. The control unit which drives the actuator to move the orthosis or prosthesis then can be operated on the basis of a result of the evaluation carried out with the evaluation unit 10.

There are a number of variants in respect of measuring the bioimpedance and evaluating the phase of the bioimpedance, which are briefly outlined below. In the following, reference is repeatedly made to the term "intersection frequency", abbreviated fs. This intersection frequency corresponds to the measurement frequency at the point of intersection 23, wherein this might be different for different muscles or different persons under certain circumstances. If necessary, this intersection frequency could be determined empirically on a case-by-case basis.

Variant 1:

The bioimpedance or the phase φ of the bioimpedance is measured at two different measurement frequencies f1 and f2, where f1 is less than fs, in particular substantially less than fs, and f2 is greater than fs, in particular substantially greater than fs. The phases φ1 and φ2 for the measurement frequencies f1 and f2, respectively, emerge from these measurements. The phases φ1 and φ2 are then compared to a reference phase φR in the evaluation unit 10. The reference phase φR could have been stored in the evaluation unit 10 in advance. In particular, the reference phase φR can be the phase φ of the bioimpedance in the relaxed muscle state, i.e., as illustrated by curve 22, 26. Even though it may be expedient to ascertain and store the reference phase φR for many different frequencies, it would also be possible to ascertain and store the reference phase φR only for the two measurement frequencies f1 and f2 to be employed.

In the evaluation unit 10, in particular by way of a comparator 13 (FIG. 1), the phases φ1 and φ2 are now compared to corresponding reference phases φR1 and φR2. Such a comparison allows a phase change or phase difference φD1 and φD2 to be ascertained. Thus, this phase change or phase difference corresponds to the change in the phases at the respective measurement frequencies caused by the muscle contraction. If the comparator 13 determines phase changes in different directions for the two measurement frequencies (or phase differences with different signs), the signal measured by the electrodes 11 is assessed as a genuine signal of a muscle contraction.

By contrast, should the comparator 13 determine phase changes in the same direction or phase differences with the same sign, the signal measured by the electrodes 11 is assessed as a disturbance signal, or at least as not belonging to a muscle contraction.

If no phase change or phase difference can be determined or if the phase change or phase difference has not exceeded a minimum value, the signal is assessed as not belonging to a muscle contraction; i.e., the measurement is preferably interpreted in this case as the muscle being in the relaxed state.

Variant 2:

The second variant differs from the first in that, in particular, one of the measurement frequencies f1, f2 is located in the vicinity of the intersection frequency fs, and in particular substantially corresponds to the intersection frequency. The evaluation is adapted accordingly. In particular, this means that a signal detected by the electrodes 11 is assessed as genuine muscle-related signal if a phase change or phase difference is determined for the measurement frequency that differs (substantially) from the intersection frequency fs while, by contrast, no or only a very small phase change or phase difference is determined for the other measurement frequency, which is close or equal to the intersection frequency fs.

By contrast, the signal is assessed as not belonging to a muscle contraction if there is no change or only a very small change in the phase for both measurement frequencies or if a phase change in the same direction emerges for both measurement frequencies.

The evaluation could be carried out merely qualitatively in the first and second variant; i.e., there could only be an ascertainment as to the directions in which the phases change (or whether a phase change is even present), without considering the magnitude of the change (any further). Such a qualitative evaluation would suffice to distinguish between a genuine muscle-related signal and a disturbance signal.

Variant 3:

This variant is similar to the second variant. In the third variant, the measurement frequencies f1 and f2 are chosen in such a way that they are either both greater than the intersection frequency fs or both less than said intersection frequency. However, in this case, one of the frequencies should be located significantly closer to the intersection frequency than the other. However, according to this variant, it would be necessary to evaluate the phase change or phase difference not only qualitatively (phase change in the same or different directions, phase differences with the same or different signs, no substantial phase change) but also quantitatively, because the expectation would be that the phases would change in the same direction at the different measurement frequencies in the case of a muscle contraction, but that the magnitude of the changes would be different.

Variant 4:

According to this variant, it is sufficient to ascertain and evaluate only one phase, i.e., carry out an ascertainment and evaluation at only one measurement frequency. Here, the measurement frequency is preferably above the intersection frequency fs and, in particular, substantially greater than the intersection frequency fs, i.e., in a frequency range for which the curve 24 (muscle contraction) is located substantially higher than the curve 26 (relaxed state) in FIG. 3. Once again, the phase change is evaluated relative to a reference phase, for example by forming a phase difference. Once again, this can be performed in the comparator 13. If the comparator 13 determines that the phase ascertained from the measurement is greater than the reference phase, the signal is assessed as belonging to a muscle contraction. Otherwise, the signal is assessed either as a disturbance signal (the phase ascertained from the measurement is less than the reference phase) or as belonging to a relaxed muscle (no phase change).

Further Explanations

It has already been mentioned that orthosis or prosthesis systems according to embodiments of the invention are able to identify genuine muscle-related signals, i.e., signals that can be traced back to a muscle contraction in particular, with greater reliability than has been possible using approaches in the prior art and, in particular, are able to distinguish said muscle signals from disturbance signals. In this context, it is advantageous to explain the profile of the absolute value |Z| of the bioimpedance or the phase φ of the bioimpedance of a possible disturbance signal. In this context, reference is made to FIGS. 4 and 5.

Figure 4:
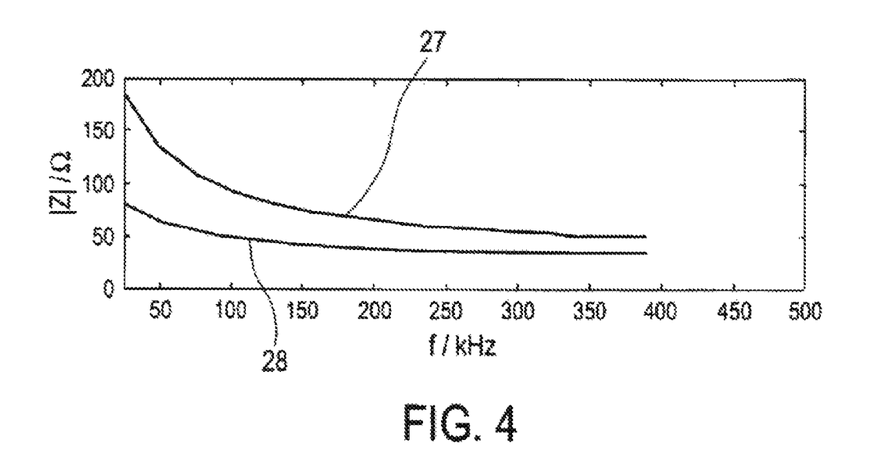
FIG. 4 shows the curve of the absolute value of a bioimpedance signal at different measurement frequencies.

FIG. 4 shows the frequency-dependent curve of the absolute value |Z| of the bioimpedance for a given muscle state. Here, the lower curve 28 shows the profile in the case of a good electrode-skin contact of the negative current electrode and curve 27 shows the profile in the case of a poor electrode-skin contact. A larger bioimpedance in terms of absolute value (upper curve 27) thus corresponds to a worse contact than a smaller bioimpedance in terms of absolute value (lower curve 28). However, an evaluation of the signals based purely on the absolute value |Z| of the bioimpedance could supply unreliable results under certain circumstances. Thus, an increase in the absolute value of the bioimpedance could either mean, for example, that the muscle has relaxed (more) in relation to a comparison state or that there has been a deterioration in the electrode-skin contact.

Figure 5:
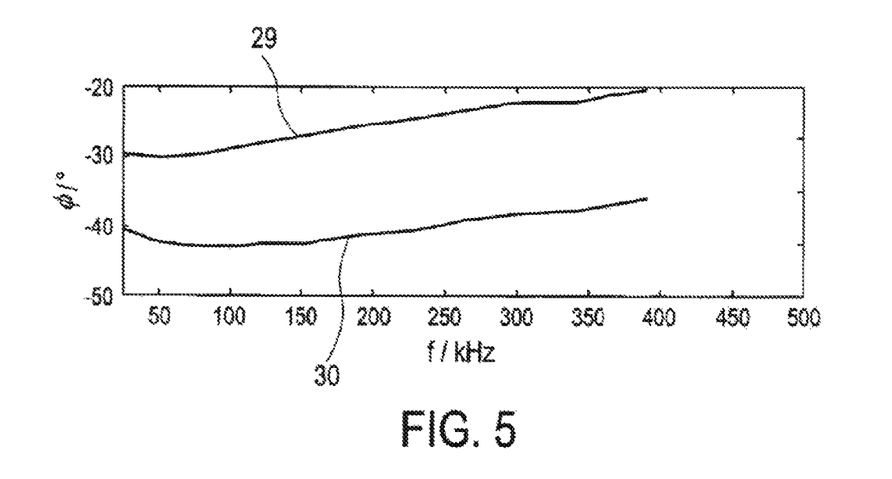
FIG. 5 shows the curve of the phase of a bioimpedance signal at different measurement frequencies.

FIG. 5 shows the frequency response of the phase of the bioimpedance in the case of a good electrode-skin contact (upper curve 29) and in the case of a poor electrode-skin contact (lower curve 30). The frequency response of the phase shown in FIG. 5 does not have the characteristic frequency response for genuine muscle-related signals as shown in FIG. 3. In particular, the curves 29 and 30 do not intersect. The differences between a genuine muscle-related signal (FIG. 3) and a disturbance signal, such as a poor electrode-skin contact (FIG. 5), for example, become particularly clear if a measurement and evaluation as per the above-described first variant is carried out. In the case of the two measurements at the two measurement frequencies f1 and f2 (with f1<fs<f2), the above-described evaluation supplies a phase change in different directions for a genuine muscle-related signal. By contrast, it supplies a phase change in the same direction for a disturbance signal such as a deterioration in the electrode-skin contact. On account of this fact, the evaluation unit 10 can distinguish between a genuine muscle-related signal and a disturbance signal.

A similar statement applies to the further above-described variants.

According to embodiments of the invention, two or more measurements can be carried out at two or more different frequencies by means of the same set of electrodes 11 (using more than one measurement channel). The measurements could be implemented virtually simultaneously, i.e., at short intervals which are not noticeable for a user. Alternatively, the measurements at the two or more different frequencies could be carried out by means of different sets of electrodes.

As shown in FIG. 1, the evaluation unit 10 as per the shown exemplary embodiment has an analog-to-digital converter (ADC) 14, which converts the ascertained phase of the bioimpedance and possibly also the absolute value of the bioimpedance and/or other measured variables or variables derived therefrom into a digital format. The digital data output by the analog-to-digital converter can be buffer-stored in a buffer 15 and, where necessary, processed further by an extended signal processing unit 16. In particular, such further processing may include controlling an actuator for the purposes of moving the orthosis or prosthesis.

FIG. 1 indicates a further advantage of embodiments of the invention. Embodiments of the invention provide for additional measurement methods and/or signal processing components only to be activated once a muscle contraction has been detected by means of the above-described methods, in particular by the comparator 13. In FIG. 1, this is indicated by an arrow which leaves the comparator 13 and leads to the symbol of an on/off switch 17 of the unit 16. Thus, processes or components which may have a comparatively high power requirement can be performed or operated in energy-saving fashion, possibly reducing the power requirement of the overall system. This may be able to save battery capacitance of the orthosis or prosthesis or of the orthosis or prosthesis system, which can also lead to benefits during the production.

According to a further embodiment of the invention, it is possible to arrange a plurality of electrode (sets) 11 in an electrode array. As a result, high geometric resolution is realizable.

Advantages (or further advantages) of at least some embodiments of the invention are the following:

It is a cost effective system, for example as a result of the fact that there is no (significantly) higher circuitry outlay in comparison with already known systems.

There is a (significant) increase in the measurement reliability of muscle contractions and better identification of the user desire following a prosthesis movement.

A small number of electrodes are required.

Possible developments/variants:

Just like the other components as well, the comparator can be realized both in digital and analog fashion.

Additionally, the method can be extended by information about the changes in absolute value of the bioimpedance during the muscle contraction.

The anisotropic impedance behavior of muscle tissue can be exploited by virtue of a plurality of (virtually) simultaneous measurements being carried out on the same muscle group in different geometric electrode arrangements.

The state of the electrode-skin transitions can be measured. From this information, it is also possible to deduce the reliability of the additional measurement of the EMG signal.

By measuring the bioimpedance, it is also possible to detect the arterial pulse wave. From this, it is possible to derive information such as heart rate, pulse wave velocity, augmentation index, blood pressure, and respiratory frequency.

The additional information arising from measuring at at least 2 frequency points supplies additional information about the contraction strength.

Possible fields of application of the invention include, inter alia, prosthetics, orthotics, human-machine-interfaces for controlling computers, machine control and the control of exoskeletons.

We claim:

1. An orthosis or prosthesis system, comprising:
at least one orthosis or prosthesis;
at least one pair of electrodes as an electrode pair configured for contacting a body of a user of the respective orthosis or prosthesis for detecting muscle-related signals;
at least one evaluation unit for muscle-related signals detected by the at least one electrode pair;
at least one actuator for moving the respective at least one orthosis or prosthesis;
at least one control unit for controlling the at least one actuator;
wherein the at least one electrode pair is configured to detect at least a first muscle-related signal using a first measurement frequency and a second muscle-related signal using a second measurement frequency;
wherein the at least one evaluation unit is configured to:
evaluate a phase of the first signal and a phase of the second signal;
compare a phase of the first signal to a reference phase in order to ascertain a first phase change;
compare a phase of the second signal to the reference phase in order to ascertain a second phase change;
evaluate the first phase change and the second phase change.

2. The orthosis or prosthesis system as claimed in claim 1, wherein the evaluation unit is configured to evaluate a phase progression of the first and second signals.

3. The orthosis or prosthesis system as claimed in claim 1, wherein the reference phase is a frequency-dependent reference phase, and evaluating the first phase change and the second phase change includes comparing the first and second phase changes.

4. The orthosis or prosthesis system as claimed in claim 3, wherein the reference phase is a phase, which substantially corresponds to a measurement in a relaxed state of a muscle.

5. The orthosis or prosthesis system as claimed in claim 4, wherein the reference phase is a phase determined in advance.

6. The orthosis or prosthesis system as claimed in claim 3, wherein the evaluation unit is configured to ascertain whether the first phase change is a phase change in the same direction as the second phase change or in an opposite direction thereto.

7. The orthosis or prosthesis system as claimed in claim 6, wherein the evaluation unit is configured to assess the first and second signals as belonging to a muscle contraction if the first and second phase changes are phase changes in opposite directions.

8. The orthosis or prosthesis system as claimed in claim 6, wherein the evaluation unit is configured to assess the first and second signals as belonging to a disturbance if the first and second phase changes are phase changes in the same direction.

9. The orthosis or prosthesis system as claimed in claim 1, wherein the first measurement frequency is more than approximately 60 kHz and the second measurement frequency is less than approximately 60 kHz.

10. The orthosis or prosthesis system as claimed in claim 1, wherein at least one of the first measurement frequency is substantially greater than 60 kHz and the second measurement frequency is substantially less than 60 kHz.

11. The orthosis or prosthesis system as claimed in claim 1, wherein the at least first and second muscle-related signals are bioimpedance signals.

12. The orthosis or prosthesis system as claimed in claim 1, wherein the at least one electrode pair is further configured to supply electrical stimulation signals to the user of the orthosis or prosthesis.

13. The orthosis or prosthesis system as claimed in claim 12, wherein the electrical stimulation signals are configured to provide the user of the orthosis or prosthesis with feedback about at least one of the movements and the state of the orthosis or prosthesis.

14. A method for open-loop or closed-loop control of an orthosis or prosthesis by an orthosis or prosthesis system as claimed in claim 1, including the steps of:
  detecting at least a first muscle-related signal, preferably a first and a second muscle-related signal, by the at least one electrode pair,
  evaluating the phase phases of at least the first muscle-related signal, preferably the phases of the at least first and the second muscle-related signal, by the at least one evaluation unit,
  controlling the at least one actuator on the basis of the result of the evaluation of the phase phases of at least the first muscle-related signal, preferably the phases of the at least first and the second muscle-related signal,
  moving the orthosis or prosthesis by way of the at least one actuator.

15. The orthosis or prosthesis system as claimed in claim 14, wherein the reference phase is a frequency-dependent reference phase.

16. An orthosis or prosthesis system, comprising:
  at least one orthosis or prosthesis;
  at least one electrode pair configured to detect at least a first muscle-related signal using a first measurement frequency and a second muscle-related signal using a second measurement frequency;
  at least one actuator to move the at least one orthosis or prosthesis;
  at least one control unit to control the at least one actuator;
  at least one evaluation unit configured to:
  evaluate muscle-related signals detected by the at least one electrode pair;
  evaluate a phase of the first muscle-related signal and a phase of the second muscle-related signal;
  compare a phase of the first signal to a reference phase in order to ascertain a first phase change;
  compare a phase of the second signal to the reference phase in order to ascertain a second phase change;
  evaluate the first phase change and the second phase change.

17. The orthosis or prosthesis system as claimed in claim 16, wherein the evaluation unit is configured to evaluate a phase progression of the first and second signal.

18. The orthosis or prosthesis system as claimed in claim 16, wherein the reference phase is a frequency-dependent reference phase, and evaluating the first phase change and the second phase change includes comparing the first and second phase changes.

19. The orthosis or prosthesis system as claimed in claim 16, wherein the reference phase is a phase, which substantially corresponds to a measurement in a relaxed state of a muscle.

20. The orthosis or prosthesis system as claimed in claim 16, wherein the evaluation unit is configured to ascertain whether the first phase change is a phase change in the same direction as the second phase change or in an opposite direction thereto.

* * * * *